United States Patent
Hanuka et al.

(10) Patent No.: US 8,864,729 B2
(45) Date of Patent: Oct. 21, 2014

(54) OSTOMY CLOSURE

(71) Applicant: Stimatix GI Ltd., Misgav Business Park (IL)

(72) Inventors: David Hanuka, Ramat-Yishai (IL); Meir Or, Kfar Eshchar (IL)

(73) Assignee: Stimatix GI Ltd., Misgav Business Park (IL)

( * ) Notice: Subject to any disclaimer, the term of this patent is extended or adjusted under 35 U.S.C. 154(b) by 0 days.

(21) Appl. No.: 13/666,461

(22) Filed: Nov. 1, 2012

(65) Prior Publication Data

US 2013/0079738 A1    Mar. 28, 2013

Related U.S. Application Data

(63) Continuation of application No. PCT/IB2011/051936, filed on May 2, 2011, and a continuation-in-part of application No. PCT/IL2010/000565, filed on Jul. 14, 2010.

(60) Provisional application No. 61/330,359, filed on May 2, 2010, provisional application No. 61/431,084, filed on Jan. 10, 2011, provisional application No. 61/225,546, filed on Jul. 14, 2009, provisional application No. 61/330,359, filed on May 2, 2010.

(51) Int. Cl.
| | |
|---|---|
| A61F 5/44 | (2006.01) |
| A61F 5/443 | (2006.01) |
| A61F 5/445 | (2006.01) |
| A61F 5/441 | (2006.01) |
| A61F 5/442 | (2006.01) |

(52) U.S. Cl.
CPC ............... *A61F 5/44* (2013.01); *A61F 5/4404* (2013.01); *A61F 5/443* (2013.01); *A61F 5/445* (2013.01); *A61F 5/441* (2013.01); *A61F 5/4407* (2013.01); *A61F 5/442* (2013.01); *A61F 2005/4455* (2013.01)
USPC .......................................................... 604/334

(58) Field of Classification Search
USPC ........................................................ 604/334
See application file for complete search history.

(56) References Cited

U.S. PATENT DOCUMENTS

| | | |
|---|---|---|
| 2,243,529 A | 5/1941 | Grossman et al. |
| 2,341,984 A | 2/1944 | Graves |

(Continued)

FOREIGN PATENT DOCUMENTS

| | | |
|---|---|---|
| CN | 1694661 | 11/2005 |
| DE | 102007062133 | 7/2009 |

(Continued)

OTHER PUBLICATIONS

Communication Relating to the Results of the Partial International Search Dated Aug. 12, 2011 From the International Searching Authority Re. Application No. PCT/IB2011/051932.

(Continued)

*Primary Examiner* — Susan Su
*Assistant Examiner* — Guy K Townsend

(57) ABSTRACT

Ostomy ports with self closing for prevention of undesired waste leakage which changing bags or covering and uncovering of a port. A valve may be automatically activated by uncovering of the port. Optionally or alternatively, a valve may be automatically opened by covering of the port.

34 Claims, 8 Drawing Sheets

(56) References Cited

U.S. PATENT DOCUMENTS

| | | | |
|---|---|---|---|
| 2,510,766 A | 6/1950 | Surface | |
| 2,544,579 A | 3/1951 | Ardner | |
| 2,639,710 A | 5/1953 | Fazio | |
| 2,667,167 A | 1/1954 | Raiche | |
| 2,971,510 A | 2/1961 | Berger | |
| 3,398,744 A | 8/1968 | Hooper | |
| 3,447,533 A | 6/1969 | Spicer | |
| 3,718,141 A | 2/1973 | Goetz | |
| 3,976,076 A | 8/1976 | Beach | |
| 4,030,500 A * | 6/1977 | Ronnquist | 604/328 |
| 4,121,589 A | 10/1978 | McDonnell | |
| 4,170,231 A | 10/1979 | Collins | |
| 4,183,357 A | 1/1980 | Bentley et al. | |
| 4,209,010 A | 6/1980 | Ward et al. | |
| 4,210,131 A | 7/1980 | Perlin | |
| 4,232,672 A | 11/1980 | Steer et al. | |
| 4,265,244 A | 5/1981 | Hill | |
| 4,338,937 A | 7/1982 | Lerman | |
| 4,344,434 A | 8/1982 | Robertson | |
| 4,351,322 A | 9/1982 | Prager | |
| 4,381,765 A | 5/1983 | Burton | |
| 4,399,809 A | 8/1983 | Baro et al. | |
| 4,534,761 A | 8/1985 | Raible | |
| 4,634,421 A | 1/1987 | Hegemann | |
| 4,642,107 A | 2/1987 | Arnone et al. | |
| 4,662,890 A | 5/1987 | Burton et al. | |
| 4,721,508 A | 1/1988 | Burton | |
| 4,786,283 A * | 11/1988 | Andersson | 604/328 |
| 4,804,375 A | 2/1989 | Robertson | |
| 4,810,250 A | 3/1989 | Ellenberg et al. | |
| 4,854,316 A | 8/1989 | Davis | |
| 4,941,869 A * | 7/1990 | D'Amico | 600/32 |
| 4,950,223 A | 8/1990 | Silvanov | |
| 4,981,465 A | 1/1991 | Ballan et al. | |
| 5,004,464 A | 4/1991 | Leise, Jr. | |
| 5,026,360 A | 6/1991 | Johnson et al. | |
| 5,045,052 A | 9/1991 | Sans | |
| 5,108,430 A | 4/1992 | Ravo | |
| 5,125,916 A | 6/1992 | Panebianco et al. | |
| 5,135,519 A | 8/1992 | Helmer | |
| 5,163,897 A | 11/1992 | Persky | |
| 5,163,930 A | 11/1992 | Blum | |
| 5,261,898 A | 11/1993 | Polin et al. | |
| 5,269,774 A | 12/1993 | Gray | |
| 5,501,678 A | 3/1996 | Olsen | |
| 5,549,588 A | 8/1996 | Johnson | |
| 5,569,216 A | 10/1996 | Kim | |
| 5,658,266 A | 8/1997 | Colacello et al. | |
| 5,683,372 A | 11/1997 | Colacello et al. | |
| 5,771,590 A | 6/1998 | Colacello et al. | |
| 5,785,677 A | 7/1998 | Auweiler | |
| 5,947,942 A | 9/1999 | Galjour | |
| 6,033,390 A | 3/2000 | von Dyck | |
| 6,050,982 A | 4/2000 | Wheeler | |
| 6,329,465 B1 | 12/2001 | Takahashi et al. | |
| 6,350,255 B1 | 2/2002 | von Dyck | |
| 6,357,445 B1 | 3/2002 | Shaw | |
| 6,481,589 B2 | 11/2002 | Blomdahl et al. | |
| 6,485,476 B1 | 11/2002 | von Dyck et al. | |
| 6,595,971 B1 | 7/2003 | von Dyck et al. | |
| 6,659,988 B1 | 12/2003 | Steer et al. | |
| 6,689,111 B2 | 2/2004 | Mulhauser et al. | |
| 6,695,825 B2 | 2/2004 | Castles | |
| 6,723,079 B2 | 4/2004 | Cline | |
| 6,963,772 B2 * | 11/2005 | Bloom et al. | 600/547 |
| 7,001,367 B2 * | 2/2006 | Arkinstall | 604/337 |
| 7,083,569 B2 | 8/2006 | Boulanger et al. | |
| 7,087,041 B2 | 8/2006 | von Dyck et al. | |
| 7,250,040 B2 | 7/2007 | Andersen | |
| 7,314,443 B2 * | 1/2008 | Jordan et al. | 600/30 |
| 7,582,072 B2 | 9/2009 | McMichael | |
| 7,670,289 B1 | 3/2010 | McCall | |
| 7,857,796 B2 | 12/2010 | Cline et al. | |
| 8,070,737 B2 | 12/2011 | Cline et al. | |
| 8,092,437 B2 | 1/2012 | Cline | |
| 8,100,875 B2 | 1/2012 | Cline et al. | |
| 8,142,406 B2 | 3/2012 | Blum | |
| 8,388,586 B2 * | 3/2013 | Weig | 604/338 |
| 8,460,259 B2 | 6/2013 | Tsai | |
| 2003/0199783 A1 * | 10/2003 | Bloom et al. | 600/549 |
| 2003/0220621 A1 | 11/2003 | Arkinstall | |
| 2004/0029467 A1 * | 2/2004 | Lacroix | 442/76 |
| 2004/0073179 A1 | 4/2004 | Andersen | |
| 2004/0122527 A1 | 6/2004 | Imran | |
| 2004/0167376 A1 | 8/2004 | Peters et al. | |
| 2004/0181197 A1 * | 9/2004 | Cline | 604/337 |
| 2005/0027159 A1 | 2/2005 | Feng et al. | |
| 2005/0054996 A1 | 3/2005 | Gregory | |
| 2005/0065488 A1 | 3/2005 | Elliott | |
| 2005/0104457 A1 * | 5/2005 | Jordan et al. | 310/36 |
| 2006/0048283 A1 * | 3/2006 | Sorensen | 2/400 |
| 2006/0206069 A1 | 9/2006 | Cline | |
| 2006/0229596 A1 | 10/2006 | Weiser et al. | |
| 2007/0049878 A1 | 3/2007 | Kim et al. | |
| 2007/0142780 A1 | 6/2007 | Van Lue | |
| 2007/0219532 A1 * | 9/2007 | Karpowicz et al. | 604/540 |
| 2007/0276346 A1 | 11/2007 | Poulsen et al. | |
| 2008/0033380 A1 | 2/2008 | Andersen | |
| 2008/0091154 A1 | 4/2008 | Botten | |
| 2008/0108862 A1 * | 5/2008 | Jordan et al. | 600/30 |
| 2008/0135044 A1 * | 6/2008 | Freitag et al. | 128/200.26 |
| 2008/0269698 A1 | 10/2008 | Alexander et al. | |
| 2008/0275410 A1 | 11/2008 | Burt | |
| 2009/0043151 A1 | 2/2009 | Gobel | |
| 2009/0216206 A1 | 8/2009 | Nishtala et al. | |
| 2009/0247969 A1 | 10/2009 | Nishtala et al. | |
| 2010/0069859 A1 | 3/2010 | Weig | |
| 2010/0174253 A1 | 7/2010 | Cline et al. | |
| 2011/0015475 A1 | 1/2011 | Hanuka et al. | |
| 2011/0040231 A1 | 2/2011 | Gregory | |
| 2011/0106032 A1 | 5/2011 | Kratky | |
| 2012/0136324 A1 | 5/2012 | Ilanuka et al. | |
| 2013/0060212 A1 | 3/2013 | Hanuka et al. | |
| 2013/0060213 A1 | 3/2013 | Hanuka et al. | |
| 2013/0079736 A1 | 3/2013 | Hanuka et al. | |
| 2013/0079737 A1 | 3/2013 | Hanuka et al. | |
| 2013/0116642 A1 | 5/2013 | Hanuka et al. | |
| 2013/0304008 A1 | 11/2013 | Hanuka et al. | |

FOREIGN PATENT DOCUMENTS

| | | | |
|---|---|---|---|
| EP | 2027835 | 2/2009 | |
| GB | 2094153 | 9/1982 | |
| JP | 2006-314479 | 11/2006 | |
| JP | 2008-507308 | 3/2008 | |
| WO | WO 87/03192 | 6/1987 | |
| WO | WO 90/07311 | 7/1990 | |
| WO | WO 96/32904 | 10/1996 | |
| WO | WO 99/43277 | 9/1999 | |
| WO | WO 01/49224 | 7/2001 | |
| WO | WO 02/058603 | 8/2002 | |
| WO | WO 03/065945 | 8/2003 | |
| WO | WO 03/071997 | 9/2003 | |
| WO | WO 2006/010556 | 2/2006 | |
| WO | WO 2008/048856 | 4/2008 | |
| WO | WO2008/103789 * | 8/2008 | A61F 13/56 |
| WO | WO 2008/141180 | 11/2008 | |
| WO | WO 2009/083183 | 7/2009 | |
| WO | WO 2009/155537 | 12/2009 | |
| WO | WO 2011/007355 | 1/2011 | |
| WO | WO 2011/138728 | 11/2011 | |
| WO | WO 2011/138731 | 11/2011 | |
| WO | WO 2013/168165 | 11/2013 | |

OTHER PUBLICATIONS

Communication Relating to the Results of the Partial International Search Dated Aug. 16, 2011 From the International Searching Authority Re. Application No. PCT/IB2011/051933.

Communication Relating to the Results of the Partial International Search Dated Nov. 17, 2010 From the International Searching Authority Re. Application No. PCT/IL2010/000565.

(56) References Cited

OTHER PUBLICATIONS

Communication Relating to the Results of the Partial International Search Dated Aug. 18, 2011 From the International Searching Authority Re: Application No. PCT/IB2011/051938.
International Preliminary Report on Patentability Dated Jun. 1, 2012 From the International Preliminary Examining Authority Re. Application No. PCT/IB2011/051933.
International Preliminary Report on Patentability Dated Jun. 5, 2012 From the International Preliminary Examining Authority Re. Application No. PCT/IB2011/051932.
International Preliminary Report on Patentability Dated Sep. 6, 2012 From the International Preliminary Examining Authority Re. Application No. PCT/IL2011/051938.
International Preliminary Report on Patentability Dated Oct. 31, 2011 From the International Preliminary Examining Authority Re. Application No. PCT/IL2010/000565.
International Search Report and the Written Opinion Dated Oct. 14, 2011 From the International Searching Authority Re. Application No. PCT/IB2011/051933.
International Search Report and the Written Opinion Dated Oct. 17, 2011 From the International Searching Authority Re. Application No. PCT/IB2011/051932.
International Search Report and the Written Opinion Dated Aug. 18, 2011 From the International Searching Authority Re. Application No. PCT/IB2011/051936.
International Search Report and the Written Opinion Dated Oct. 19, 2011 From the International Searching Authority Re: Application No. PCT/IB2011/051938.
International Search Report and the Written Opinion Dated Feb. 28, 2011 From the International Searching Authority Re. Application No. PCT/IL2010/000565.
Invitation to Pay Additional Fees Dated Oct. 7, 2011 From the International Preliminary Examining Authority Re. Application No. PCT/IL2010/000565.
Notification Concerning Informal Communications With the Applicant Dated May 3, 2012 From the International Searching Authority Re: Application No. PCT/IB2011/051938.
Notification Concerning Informal Communications With the Applicant Dated May 4, 2012 From the International Searching Authority Re: Application No. PCT/IB2011/051933.
Notification Concerning Informal Communications With the Applicant Dated May 18, 2012 From the International Searching Authority Re: Application No. PCT/IB2011/051932.
Response Dated May 30, 2011 to the Written Opinion of Feb. 28, 2011 From the International Searching Authority Re. Application No. PCT/IL2010/000565.
Restriction Official Action Dated Oct. 15, 2012 From the US Patent and Trademark Office Re. U.S. Appl. No. 12/835,838.
Written Opinion Dated Jun. 1, 2012 From the International Preliminary Examining Authority Re. Application No. PCT/IB2011/051938.
Communication Pursuant to Article 94(3) EPC Dated Feb. 11, 2013 From the European Patent Office Re. Application No. 10747082.5.
Official Action Dated Jan. 30, 2013 From the US Patent and Trademark Office Re. U.S. Appl. No. 12/835,838.
Official Action Dated Mar. 25, 2013 From the US Patent and Trademark Office Re. U.S. Appl. No. 13/666,178.
International Preliminary Report on Patentability Dated Nov. 15, 2012 From the International Bureau of WIPO Re. Application No. PCT/IB2011/051936.
Official Action Dated Mar. 5, 2013 From the US Patent and Trademark Office Re. U.S. Appl. No. 13/666,513.
Translation of Notification of Office Action Dated Jul. 30, 2013 From the State Intellectual Property Office of the People's Republic of China Re. Application No. 201080032032.X.
Official Action Dated Aug. 29, 2013 From the US Patent and Trademark Office Re. U.S. Appl. No. 12/835,838.
Official Action Dated Jul. 1, 2013 From the US Patent and Trademark Office Re. U.S. Appl. No. 13/384,343.
Applicant-Initiated Interview Summary Dated Jul. 25, 2013 From the US Patent and Trademark Office Re. U.S. Appl. No. 13/680,161.
Applicant-Initiated Interview Summary Dated Jul. 26, 2013 From the US Patent and Trademark Office Re. U.S. Appl. No. 13/666,513.
Applicant-Initiated Interview Summary Dated Jul. 26, 2013 From the US Patent and Trademark Office Re. U.S. Appl. No. 13/680,169.
Official Action Dated Jul. 10, 2013 From the US Patent and Trademark Office Re. U.S. Appl. No. 13/680,169.
Official Action Dated Jul. 11, 2013 From the US Patent and Trademark Office Re. U.S. Appl. No. 13/680,161.
Communication Relating to the Results of the Partial International Search Dated Sep. 16, 2013 From the International Searching Authority Re. Application No. PCT/IL2013/050401.
Official Action Dated Oct. 16, 2013 From the US Patent and Trademark Office Re. U.S. Appl. No. 13/666,244.
Official Action Dated Oct. 16, 2013 From the US Patent and Trademark Office Re. U.S. Appl. No. 13/666,513.
Official Action Dated Oct. 18, 2013 From the US Patent and Trademark Office Re. U.S. Appl. No. 13/384,343.
Applicant-Initiated Interview Summary Dated Dec. 13, 2013 From the US Patent and Trademark Office Re. U.S. Appl. No. 13/666,244.
Applicant-Initiated Interview Summary Dated Dec. 13, 2013 From the US Patent and Trademark Office Re. U.S. Appl. No. 13/666,513.
Communication Pursuant to Article 94(3) EPC Dated Dec. 17, 2013 From the European Patent Office Re. Application No. 11723672.9.
Communication Pursuant to Article 94(3) EPC Dated Dec. 19, 2013 From the European Patent Office Re. Application No. 11723674.5.
Communication Pursuant to Article 94(3) EPC Dated Dec. 19, 2013 From the European Patent Office Re. Application No. 11724783.3.
International Search Report and the Written Opinion Dated Dec. 20, 2013 From the International Searching Authority Re. Application No. PCT/IL2013/050401.
Official Action Dated Nov. 7, 2013 From the US Patent and Trademark Office Re. U.S. Appl. No. 13/666,178.
Official Action Dated Nov. 7, 2013 From the US Patent and Trademark Office Re. U.S. Appl. No. 13/680,169.
Official Action Dated Jan. 14, 2014 From the US Patent and Trademark Office Re. U.S. Appl. No. 13/680,161.
Summons to Attend Oral Proceedings Pursuant to Rule 115(1) EPC Dated Nov. 22, 2013 From the European Patent Office Re. Application No. 10747082.5.
Advisory Action Before the Filing of an Appeal Brief Dated Feb. 4, 2014 From the US Patent and Trademark Office Re. U.S. Appl. No. 12/835,838.
Advisory Action Before the Filing of an Appeal Brief Dated Mar. 31, 2014 From the US Patent and Trademark Office Re. U.S. Appl. No. 13/384,343.
Applicant-Initiated Interview Summary Dated Jan. 27, 2014 From the US Patent and 'Trademark Office Re. U.S. Appl. No. 13/384,343.
Notice of Allowance Dated Apr. 4, 2014 From the US Patent and Trademark Office Re. U.S. Appl. No. 13/680,169.
Notice of Allowance Dated Feb. 18, 2014 From the US Patent and Trademark Office Re. U.S. Appl. No. 13/666,513.
Notice of Allowance Dated Mar. 18, 2014 From the US Patent and Trademark Office Re. U.S. Appl. No. 13/666,178.
Applicant-Initiated Interview Summary Dated Apr. 14, 2014 From the Re. U.S. Appl. No. 13/384,343.
Notice of Allowance Dated Apr. 29, 2014 From the Re. U.S. Appl. No. 13/680,161.
Notice of Reason for Rejection Dated Apr. 15, 2014 From the Japanese Patent Office Re. Application No. 2012-520149 and Its Translation into English.
Notification of Office Action Dated May 6, 2014 From the State Intellectual Property Office of the People's Republic of China Re. Application No. 2011800331827 and Its Translation Into English.

(56) References Cited

OTHER PUBLICATIONS

Notification of Office Action Dated Apr. 18, 2014 From the State Intellectual Property Office of the People's Republic of China Re. Application No. 201080032032.X and Its Translation Into English.
Search Report Dated May 6, 2014 From the State Intellectual Property Office of the People's Republic of China Re. Application No. 2011800331827 and Its Translation Into English.

Search Report Dated Apr. 18, 2014 From the State Intellectual Property Office of the People's Republic of China Re. Application No. 201080032032.X and Its Translation Into English.
Notification of Office Action Dated May 27, 2014 From the State Intellectual Property Office of the People's Republic of China Re. Application No. 201180033162.X.
Official Action Dated Jun. 26, 2014 From the Re. U.S. Appl. No. 13/384,343.

* cited by examiner

OSTOMY CLOSURE

RELATED APPLICATIONS

This application is a Continuation of PCT Patent Application No. PCT/IB2011/051936 filed on May 2, 2011, which claims the benefit of priority under 35 USC 119(e) of U.S. Provisional Patent Application Nos. 61/330,359 filed on May 2, 2010 and 61/431,084 filed on Jan. 10, 2011.

PCT Patent Application No. PCT/IB2011/051936 is also a Continuation-In-Part (CIP) of PCT Patent Application No. PCT/IL2010/000565 filed Jul. 14, 2010, which claims the benefit of priority under 35 USC §119(e) of U.S. Provisional Patent Application Nos. 61/225,546 filed on Jul. 14, 2009 and 61/330,359 filed on May 2, 2010. The contents of the above applications are all incorporated by reference as if fully set forth herein in their entirety.

PCT Patent Application No. PCT/IB2011/051936 is also related to PCT Patent Application Nos. PCT/IB2011/051932, PCT/IB2011/051938, and PCT/IB2011/051933, which were all filed by, inter alia, Applicant Stimatix GI Ltd., concurrently with PCT Patent Application No. PCT/IB2011/051936, the disclosures of which are incorporated herein by reference.

FIELD AND BACKGROUND OF THE INVENTION

The present invention, in some embodiments thereof, relates to ostomy ports and, more particularly, but not exclusively, to an ostomy bag replacement mechanism for use in an ostomy port.

Ostomy bags are generally used to collect waste contents discharged through a stoma. Occasionally, the stoma includes an ostomy port to which the bag is attached and through which the waste is discharged. The bags are generally recommended to be replaced when they are one third to one half full to avoid applying excessive pressure to the stomal area and/or to tissue and organs in the abdominal cavity to which the port may be attached, and to prevent possible leakage from the bag. When replacing the bag, waste content remaining inside the ostomy port may flow out and cause possible risk of skin irritation, as well as discomfort and embarrassment to a user of the port. Methods and devices have been described for dealing with undesired waste content flow from ostomy ports, some of which are cited below.

U.S. Pat. No. 6,033,390 relates to "a continent ostomy port device has a face plate defining an aperture alignable with the opening of a stoma in the user's body and a closure adjacent to the aperture is adapted to permit covering and uncovering of the aperture in the face plate. A catheter extends from one side of the face plate proximally, and one end of the catheter is disposed within the ostomy site when the port device is in use. The catheter has continuous exterior and interior side walls, the latter defining a major lumen and is sized and shaped for non-surgical insertion through a stoma to a sufficient distance that the presence of the catheter within the stoma provides a barrier which reduces the incidence of prolapse, without the use of extraneous, externally applied materials or additional surgery. A removable cartridge fits snugly and slideably within the major lumen of the catheter of the device so as to prevent inadvertent escape of body waste material from the stoma when the cartridge is in place, without use of an ostomy bag, and to clean the interior side wall of the catheter as the cartridge is pressed into the major lumen. An anti-reflux valve is activated to prevent escape of body waste and deactivated for passage of fluid. Retaining structure is connected to the catheter, and is non-surgically, snugly fittable into the stoma, to cause the port device to be self-retaining in a normal use position within a stoma, without surgery or fixation materials."

U.S. Pat. No. 5,569,216 relates to "a multipurpose colostomy device for fixing in the stoma or rectum of a human body, includes an internal balloon, a ring configured external balloon surrounding the internal balloon, a connecting tube disposed under the both internal and external balloons, a joint tube operatively connected to a drainage hose and disposed under connecting tube, a supporting plate disposed between the connecting and joint tubes for fixing the colostomy to the abdominal wall, and an L-shaped supply tube containing a pair of air passages, a washing fluid passage and an enema fluid passage."

U.S. Pat. No. 4,634,421 relates to "a continent ostomy valve comprising a drainage tube which is secured at one end within the stoma of the patient while the other end passes through an orifice in a disk-shaped valve body which includes releasable clamping means for selectively occluding the drainage tube. The outer end of the drainage tube is stored on the face of the valve body under a cover which encloses the valve body and provides a low profile of uniform configuration.

Additional background art includes U.S. Pat. Nos. 6,527,755; 5,197,984; U.S. Patent Application Publication No. 2006/018995 A1; and U.S. Patent Application Publication No. 2009/0227971.

SUMMARY OF THE INVENTION

There is provided in accordance with an exemplary embodiment of the invention a ostomy port comprising a waste channel and a valve for selectively blocking and unblocking said waste channel, wherein said valve is configured to be activated to change a state by one or both of the covering or uncovering of said channel. Optionally, said valve comprises a shutter valve which is opened by axial force along said channel in a direction towards the body. Optionally or alternatively, said valve comprises a plurality of flaps.

In an exemplary embodiment of the invention, said valve comprises an expandable element. Optionally, said port includes one or both of a reservoir of fluid and a pump for causing an inflation chamber associated with said expandable element.

In an exemplary embodiment of the invention, said valve is configured to automatically block said channel when a cover or bag on said channel are removed. Optionally, said cover or bag include a tube which, when inserted into said channel, open said valve and when removed form said channel allow said valve to self-close.

In an exemplary embodiment of the invention, said valve is automatically activated to unblock said channel when said channel is covered by a suitable cover or bag.

In an exemplary embodiment of the invention, the port comprises a manual actuator for one or both of opening and closing said valve.

In an exemplary embodiment of the invention, said bag is in fluid communication with said waste conduit and an inside of a body in which said port is fitted.

In an exemplary embodiment of the invention, said valve is designed to resist a force exerted in a proximal direction by waste content in said waste channel.

In an exemplary embodiment of the invention, said valve is designed to open away from the body when a force exerted in a proximal direction by waste content in said waste channel is higher than a safety threshold. Optionally, said threshold is between 70 and 200 mmHg There is provided in accordance with an exemplary embodiment of the invention a method for regulating waste content flow through a waste channel in an ostomy port comprising:

(a) closing a valve to block said channel; and (b) uncovering a proximal opening of said channel. Optionally, closing a valve comprises automatically closing said valve by said uncovering. Optionally or alternatively, said port has a cover including an elongate element which maintains said valve in an open configuration when inserted in said channel, and wherein said uncovering retracts said elongate element and allows said valve to close. Optionally, the method comprises attaching a bag or a cover to said port, said attaching automatically reopening said valve.

In an exemplary embodiment of the invention, the method comprises manually closing said valve.

In an exemplary embodiment of the invention, the method comprises irrigating said waste channel.

There is provided in accordance with an exemplary embodiment of the invention an ostomy port having a waste channel, comprising:

an inflatable section inside said waste channel, said section being inflatable to a degree sufficient to block said channel and deflectable to a degree whereby it does not block or interfere with flow in said channel; and an integral inflator configured for selectively inflating said inflatable section to said blocking state.

In an exemplary embodiment of the invention, the port comprises a stomal cover and wherein said inflator is provided in or on said stomal cover. Optionally or alternatively, the port comprises a check valve for regulating a pressure in said inflatable section. Optionally, said check valve is suitable for deflation of said inflatable section.

In an exemplary embodiment of the invention, the port comprises a reservoir for holding inflation fluid for said inflatable section.

In an exemplary embodiment of the invention, said inflator comprises an air pump.

In an exemplary embodiment of the invention, the port comprises a deflation valve.

In an exemplary embodiment of the invention, said inflator is electrically operated and activated by one or both of covering and uncovering of said port, using a covering or uncovering sensing circuit.

In an exemplary embodiment of the invention, the port comprises an indicator indicating one or both of when said channel is blocked and when said channel is open. Optionally, said indicator is a visual or acoustic display electrically activated by a sensing element which senses a state of said valve.

In an exemplary embodiment of the invention, said inflator is electrically operated and including a battery for powering said electrically operated inflator.

In an exemplary embodiment of the invention, said inflator is adapted to be manually operated.

There is provided in accordance with an exemplary embodiment of the invention an ostomy port, comprising:

(a) a waste channel;

(b) a valve mechanism in said waste channel comprising a conduit section having a twistable section; and (c) a flange configured for selectively maintaining said conduit section in a twisted position.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
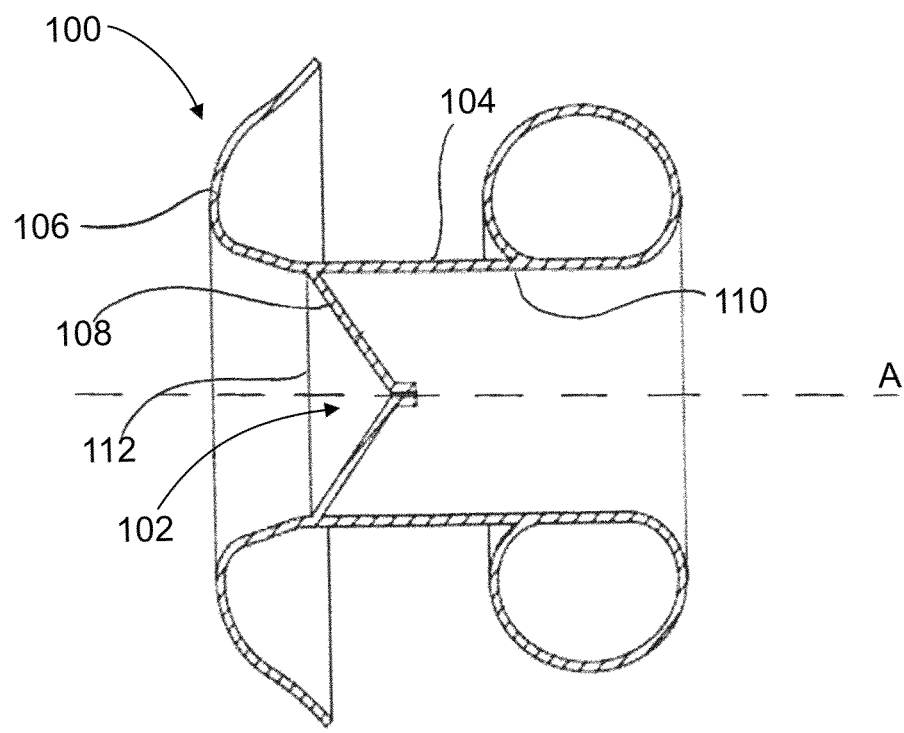
FIGS. 1A and 1B schematically illustrate an exemplary valve mechanism including a shutter for sealing a proximal opening of an ostomy port in a closed mode and open mode, respectively, according to an embodiment of the present invention.

The present invention, in some embodiments thereof, relates to ostomy ports and, more particularly, but not exclusively, to an ostomy bag replacement mechanism for use in an ostomy port.

Reference hereinafter to an ostomy port or a stomal cover may include any of the embodiments described in any one of the applications from which this disclosure is claiming benefit and referenced in the above section Related Application.

An aspect of some embodiments of the present invention relates to a valve mechanism inside an ostomy port configured to block a proximal opening of the port when the opening is uncovered, and to unblock the proximal opening when covered.

In some exemplary embodiments, the valve mechanism includes a blocking element which is retracted for unblocking the proximal opening. In alternate embodiments, the blocking element is deflated for unblocking the proximal opening. In other alternate embodiments, the blocking element is untwisted for unblocking the proximal opening. The valve mechanism includes two states, a default mode wherein the blocking element is deployed and waste flow is substantially blocked from reaching the proximal opening, and an open mode wherein a flow path is opened for the waste content to flow through the proximal opening.

As used hereinafter, distal refers to a direction away from the proximal opening and towards an interior of the abdominal cavity while proximal refers to a direction away from the abdominal cavity towards the proximal opening.

In some exemplary embodiments, the blocking element includes one or more bendable flaps, for example, 2, 3, 4, 5, or more. In the closed mode, the flaps resist pressure applied in a proximal direction, for example, due to waste content pushing on the shutter. In the open mode, the flaps are bendable in the distal direction, pushed by an elongate element (termed herein "cannula" as it is hollow in some embodiments, to allow waste passage therethrough) inserted through the proximal opening in a distal direction past the flaps. Optionally, the flaps are pushed by the cannula so that they abut an inner wall of the port. Optionally, waste content behind the flaps is pushed in a distal direction by the applied force of the cannula.

In some exemplary embodiments, the flaps are made from an elastic and flexible material, for example silicone rubber. Optionally, the flaps are made from a same material as the ostomy port. Exemplary parameters are as follows. A flap thickness may range, from 0.2-3 mm, for example, 1 mm, 1.5 mm, 2 mm. A flap durometer may range from 10-100 Shore A, for example, 40 Shore A, 55 Shore A, 75 Shore A. In some exemplary embodiments, the pliability of the flaps, determined by a combination of their thickness and durometer, is such that they conform to the shape of the inner wall as they bend in a distal direction. In the closed mode, the flaps may be oriented at an angle relative to an axis of the ostomy port ranging from about 30° up to 90° (perpendicular to the axis), for example, 45°, 60°, 80°. Optionally, the pliability of the flaps enable the valve mechanism, in the closed mode, to retain liquid or semi-liquid waste inside the ostomy port when the pressure in the waste is higher than the ambient pressure, for example by 5 mmHg, 10 mmHg, 20 mmHg, 30 mmHg, 40 mmHg, 50 mmHg In some exemplary embodiments, the flaps are molded integrally as part of the ostomy port. Alternatively, the flaps are attached to the inner wall using methods known in the art, for example bonding or welding. Optionally, the flaps have a reduced thickness at their connection region with the inner wall to facilitate their bending in the distal direction towards the inner wall. Optionally, the flaps overlap one another in the closed mode blocking the opening.

In some embodiment, the cannula is adapted to transport waste content from a distal section of the ostomy port through the open flaps through the proximal opening. The cannula, in some embodiments, is attached to an ostomy bag for receiving the waste content flowing therethrough. Alternatively, the cannula is sealed at a proximal end and acts as a plug retaining the waste content inside the ostomy port. Alternatively, the cannula includes a flexible proximal portion through which the waste content may be discharged into a water closet (toilet) or an ostomy bag or other receptacle. Removal of the conduit will cause the valve to return to the closed mode, blocking waste content flow.

In some exemplary embodiments, the blocking element includes a constricted elastic portion in an ostomy port. The elastic portion is constricted in the default mode, which may be particularly useful for use with an ileostomy where semi-liquid waste content is relatively common. For example, the ostomy port wall durometer may range from 10-100 Shore A, for example, 30 Shore A, 50 Shore A, 70 Shore A. The wall thickness may range, for example, from 0.3-2 mm. Optionally, the semi-liquid waste content remains in a section of the port distal to the constriction. Optionally, solid waste remains in the section distal to the constriction. Insertion of the cannula past the constriction temporarily removes the blocking for allowing passage of the waste content from the distal section to the proximal opening. Withdrawing the cannula proximally to the constriction renews blocking of waste content. Alternatively, the constriction is not part of the ostomy port and is created by attaching a clamp to an exterior of an elastic portion of the port. Removal of the clamp removes the blocking.

In some exemplary embodiments, the blocking element includes an inflatable section in the ostomy port. Optionally, the blocking element includes two inflatable sections in the port. Optionally, the inflatable section includes an elastic balloon. An inflator in the stomal cover and in fluid communication with the inflatable section through a lumen is used for inflating the section.

In some exemplary embodiments, an inflation section inflation volume may be, for example, between 5-30 ml for colostomy, and between 1-10 ml for ileostomy and urostomy. An inflation section inflation pressure may be between 1-50 mmHg An inflation lumen diameter may range from 0.5-3 mm. An inflation section wall thickness may range from 0.3-1 mm.

In some exemplary embodiments, an inflation fluid used by the inflator to inflate the inflatable section is air. Alternatively, the inflation fluid is a liquid, such as, for example, water. A check valve is connected between the inflator and the inflatable section for retaining the air pressure in the section at least for a predetermined period of time, for example, between 10 and 60 seconds, between 1-10 minutes or longer. Optionally, the check valve is part of the inflator. Alternatively, the check valve is in the lumen. The predetermined period of time is a time required to replace the bag, and is greater than 1 minute, for example, 2 minutes, 3 minutes, 5 minutes, 7 minutes, or greater, even up to 30 minutes. Optionally, the check valve allows reflux of inflation fluid so that the inflatable section empties through the check valve. Additionally or alternatively, a user-activated valve is included in the stomal cover for emptying the inflatable section.

In some exemplary embodiments, the inflator includes an internal volume sufficient to store an amount of inflation fluid (air or liquid) required to inflate the inflatable section. Optionally, the inflator is elastic. Additionally or alternatively, the inflator includes foam inside the volume which provides elasticity. In some embodiments, a reservoir is included in the stomal cover for storing inflation fluid. Alternatively, the reservoir is attached to the user's body. Optionally, the volume of the inflator and/or the volume of the reservoir are in the range from 5 ml-35 ml, for example, 10 ml-30 ml, 15 ml-30 ml, 15 ml-25 ml. Additionally or alternatively, for air as an inflation fluid, a second check valve is used supplying air to the inflator from the ambient.

In some exemplary embodiments, the inflator is manually operated by a user of the ostomy port, for example, through a manual pumping action. Additionally or alternatively, the inflator is electrically operated requiring that the user only activate an electric switch. Optionally, a DC power source (battery) for driving the inflator is located in the stomal cover. Alternatively, the DC power source is adhered to the user's body. Additionally or alternatively, inflation is automatically responsive to a high pressure signal from a pressure sensing mechanism in the port and/or to a signal from a controller regarding deployment of an ostomy bag. Additionally or alternatively, the pressure sensing mechanism senses an increase in pressure inside the ostomy port and provides an indication to the user. The indication may be a protruding element which may be seen and/or felt by the user, or an electrical or electromechanical indication such as, for example, a light, a vibration, a sound.

In some exemplary embodiments, the blocking element includes a twisted elastic portion in the ostomy port. In the closed mode, the elastic portion remains in a twisted state preventing waste content flow to the proximal opening. Untwisting the elastic portion switches the valve to the open state. The blocking element may be maintained in the closed mode by removably affixing the stomal cover, which is twisted together with a proximal section of the twisted portion relative to a distal section, to a flange attached to the user's abdomen adapted to prevent untwisting of the stomal cover. Releasing the stomal cover from the flange untwists the stomal cover and the elastic portion. Attachment of the flange and the stomal cover includes use of mating fasteners.

In some exemplary embodiments, the flange is thin and flexible for user comfort. The flange may be made from plastics or elastomers. Pins attaching the stomal cover to the flange may be rigid, semi-rigid or slightly pliable (as, e.g., in 80 Shore A silicone rubber), and may be from a plastic or elastomer. Stomal cover twisting may range from 45° to 540°.

In some exemplary embodiments, a pressure sensor (not shown) is assembled in an interior of the ostomy port, for example on an internal wall of the ostomy port, and a control unit is assembled at a portion of the ostomy port externally to the user's body, for example on the stomal cover. The control unit receives pressure signals from said pressure sensor, and is programmed with a logic algorithm for selectively opening a gas release valve upon fulfillment of predetermined conditions, for example any of the following conditions:

a. Internal pressure is greater than 60 mmHg for more than 1 min;
 b. Internal pressure is greater than 100 mmHg for more than 10 sec;
 c. Internal pressure is greater than 150 mmHg, immediate release.

Optionally, the ostomy port is equipped with an indication mechanism, for example visual, audible and/or vibrational alarm and/or a wireless transmitter (e.g., Bluetooth), to notify the user of an activation of the gas release valve.

Additionally or alternatively, the control unit notifies the user on a need to release gas without automatically activating the gas release valve. Optionally, the gas release valve can be closed either manually by the user or automatically by said control unit when the internal pressure decreases, for example, to no greater than 30 mmHg.

In some exemplary embodiments, a pressure sensor and a control unit as those described above control the opening of a gas release valve and/or deploying of a disposable collection bag, according to a predetermined logic, for example:

a. As internal pressure is greater than 60 mmHg for more than 1 min, open the gas release valve;
 b. As internal pressure is greater than 60 mmHg for more than 2 min, deploy the disposable collection bag;
 c. As internal pressure is greater than 100 mmHg for more than 10 sec, open the gas release valve;
 d. As internal pressure is greater than 100 mmHg for more than 30 sec, deploy the disposable collection bag;
 e. As internal pressure is greater than 150 mmHg, open the gas release valve immediately;
 f. As internal pressure is greater than 150 mmHg, deploy the disposable collection bag immediately;

Optionally, the pressure sensor includes a mechanical or electro-mechanical control. Additionally or alternative, the pressure sensor may include an override mechanism for allowing the user to decide to open the gas release valve when alerted that the internal pressure has exceeded the predetermined levels. Optionally, the gas release valve can be closed either manually by the user or automatically by a controller when the internal pressure decreases to no greater than 30 mmHg if the ostomy bag has not been deployed.

In some exemplary embodiments, any of the previously described valve mechanisms may be used with an intestinal pouch. Optionally, the intestinal pouch is a Koch pouch. Alternatively, the intestinal pouch is an Indiana pouch.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Figure 1B:
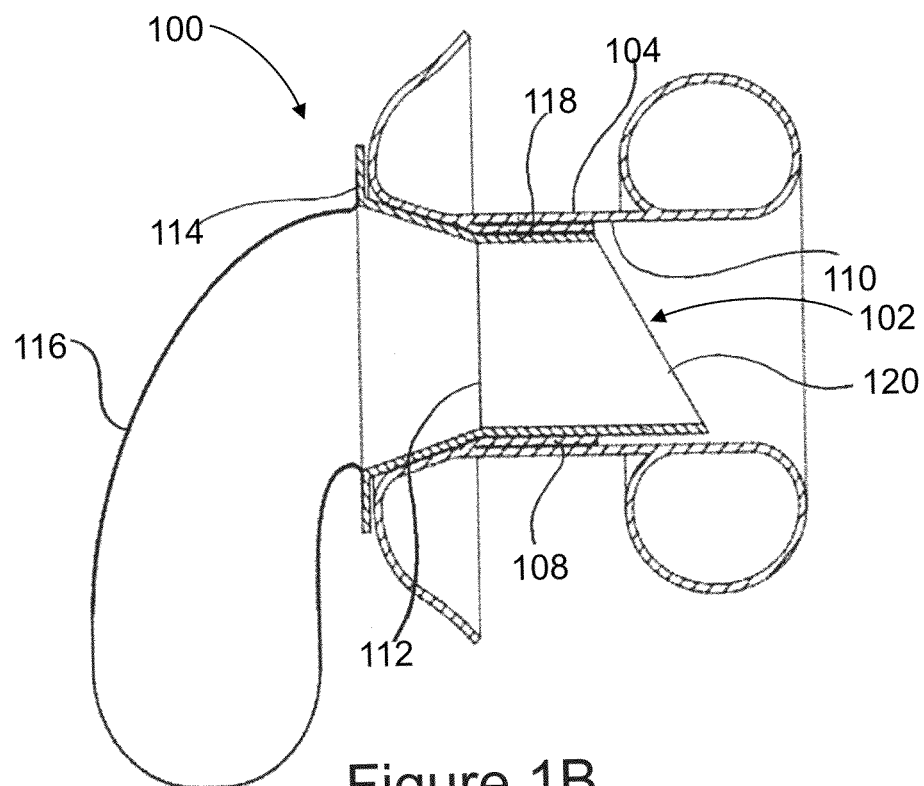
Figure 1C:
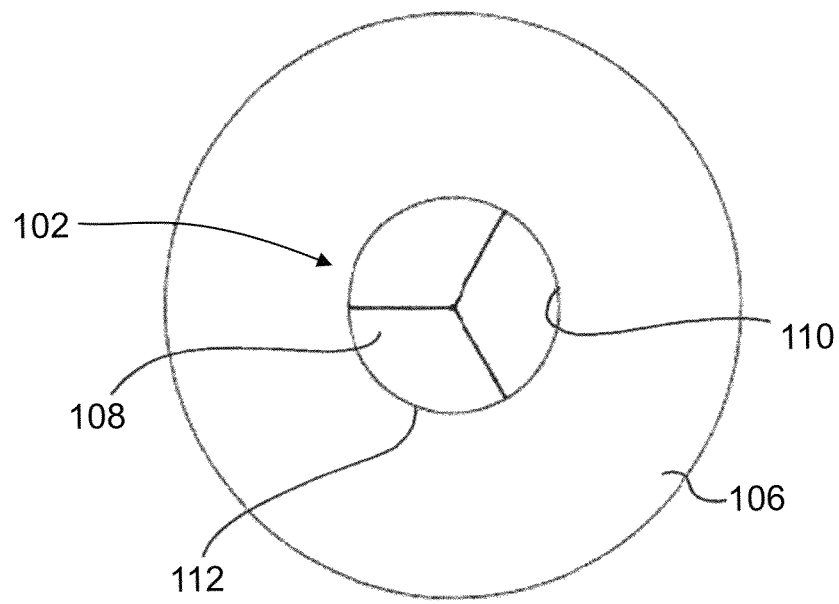
FIG. 1C schematically illustrates a view of the shutter in the closed mode as viewed through the proximal opening, according to some embodiments of the present invention.

Reference is made to FIGS. 1A and 1B which schematically illustrate an exemplary valve mechanism 100 including a blocking element 102 for sealing a proximal opening 112 of an ostomy port 104 in a closed mode and an open mode, respectively, according to an embodiment of the present invention. Optionally, valve mechanism 100 is used with an ostomy port 104 having a stomal cover 106. Reference is also made to FIG. 1C which schematically illustrates a view of blocking element 102 in closed mode as viewed through proximal opening 112, according to some embodiments of the present invention. In the embodiment shown, blocking element 102 includes three flaps 108 equally spaced along a circumference of an inner wall 110 in ostomy port 104. Optionally, less than 3 flaps 108 may be used. Alternatively, more than 3 flaps may be used.

In FIG. 1A, ostomy port 104 is shown with blocking element 102 in the closed mode sealing proximal opening 112 to prevent waste content from flowing out the proximal opening. Optionally, proximal opening 112 is sealed as an ostomy bag attached to ostomy port 104 is being replaced. Flaps 108 are upwardly disposed from inner wall 110 towards a center axis A of the port, and angularly oriented away from proximal opening 112. Optionally, flaps 108 are angularly oriented away from proximal opening 112 to facilitate their bending in a distal direction towards inner wall 110. Additionally or alternatively, flaps 108 are angularly oriented away from proximal opening 112 to provide resistance to pressure in a proximal direction from the waste content. Alternatively, flaps 108 lie in a plane perpendicular to the center axis A.

In FIG. 1B, ostomy port 104 is shown in the open mode with a cannula 118 inserted in proximal opening 112, an ostomy bag 116 attached to the cannula. Optionally, cannula 118 is part of a cap 114 which seals proximal opening 112 and includes deployable ostomy bag 116. Additionally or alternatively, a flexible sleeve or catheter (not shown) is attached to the cannula, enabling the diversion of fecal matter directly into the toilet or other means of waste collection. Cannula 118 is cylindrically-shaped and penetrates distally into ostomy port 104, opening blocking element 102 by pushing flaps 108 against inner wall 110. Optionally, cannula 118 includes a sloped leading edge 120 for facilitating pushing on flaps 108 causing them to bend. Alternatively, distal end 120 does not include the sloped opening rather the opening lies in a plane perpendicular to the center axis A (in FIG. 1A). Optionally, with blocking element 102 open, waste content may flow through cap 114, including through cannula 118, into deployed ostomy bag 116. Optionally, removing cap 114 from proximal opening 112 returns flaps 108 to the closed position due to their elasticity, preventing waste content from reaching proximal opening 112.

Figure 2:
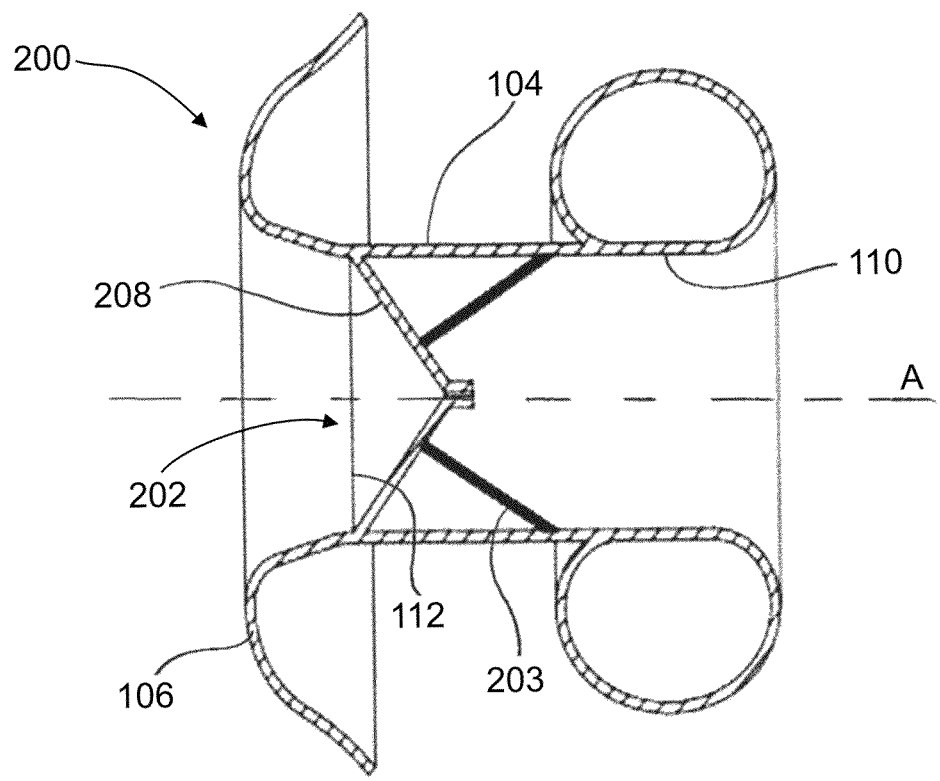
FIG. 2 schematically illustrates an exemplary valve mechanism including a reinforced shutter for sealing the proximal opening in the ostomy port, according to some embodiments of the present invention.

Reference is now also made to FIG. 2 which schematically illustrates an exemplary valve mechanism 200 including a reinforced blocking element 202 for sealing proximal opening 112 in ostomy port 104, according to some embodiments of the present invention. Optionally, valve mechanism 200 is used with ostomy port 104 having stomal cover 106. Optionally, proximal opening 112 is sealed while replacing an ostomy bag attached to ostomy port 204.

Reinforced blocking element 202 includes flaps 208 disposed from inner wall 110 towards the center axis A of the port, and angularly oriented away from the proximal opening. Optionally, flaps 208 are angularly oriented away from proximal opening 112 to facilitate their bending in a distal direction towards inner wall 110. Alternatively, flaps 108 lie in a plane perpendicular to the center axis A (in FIG. 1A). Blocking element 202 includes supports 203 connecting flaps 208 to inner wall 110, adapted to resist the pressure of waste content pushing on flaps 208 in the proximal direction when blocking element 202 is closed. Supports 203 may include flexible, non-stretchable cords, and may be of a biocompatible material. Supports 203 may have, for example, a characteristic transverse dimension (e.g. diameter if the cross section is circular) ranging from 0.2 mm-2 mm Alternatively, supports 203 in combination with the angular orientation of flaps 208 resist the pressure Optionally, flaps 208 are substantially more pliable than flaps 108 of FIGS. 1A and 1B, hence reducing the force needed to be applied in order to open blocking element 202 . Optionally, flaps 208 display a film-like behavior having a reduced resistance to bending. Optionally, supports 203 are cords. Optionally, supports 203 are made from a flexible non-stretchable material.

In some exemplary embodiments, reinforced blocking element 202 is opened by inserting cannula 118 (not shown in FIG. 2) through proximal opening 112. Optionally, cannula 118 is part of cap 114 (not shown FIG. 2). Cannula 118 penetrates distally into ostomy port 104 opening blocking element 202 by pushing flaps 208 against inner wall 110. Optionally, with blocking element 202 open, waste content may flow through cap 114, including through cannula 118, into deployed ostomy bag 116. Optionally, removal of cap 114 from proximal opening 112 returns flaps 208 to substantially the same default upright closed position preventing waste content from reaching proximal opening 112. Additionally or alternatively, pressure exerted by waste matter in the ostomy port's interior returns flaps 208 to the default upright closed position.

Figure 3A:
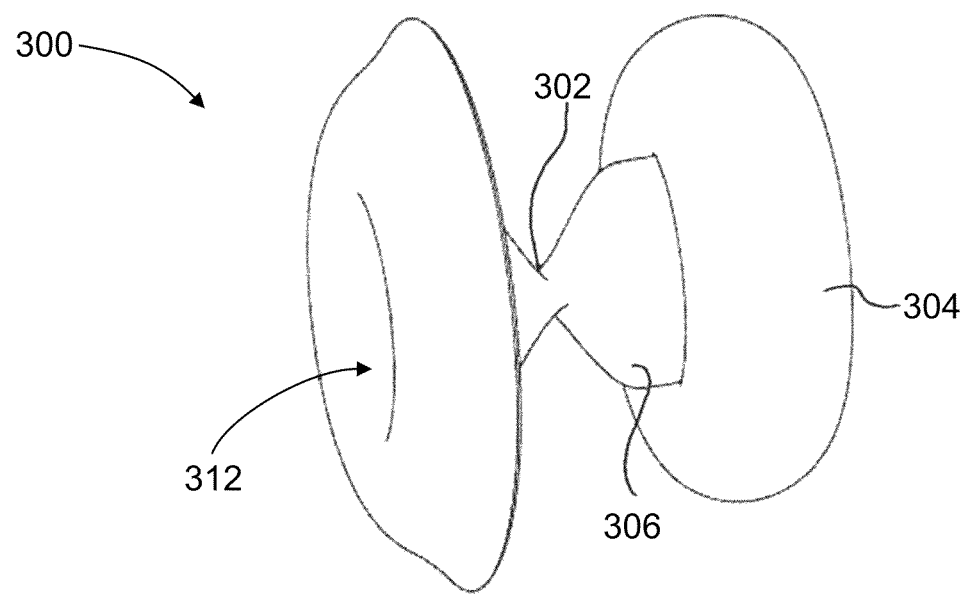
FIG. 3A schematically illustrates an exemplary valve mechanism including an elastically constricted portion in an ostomy port, according to another embodiment of the present invention.
Figure 3B:
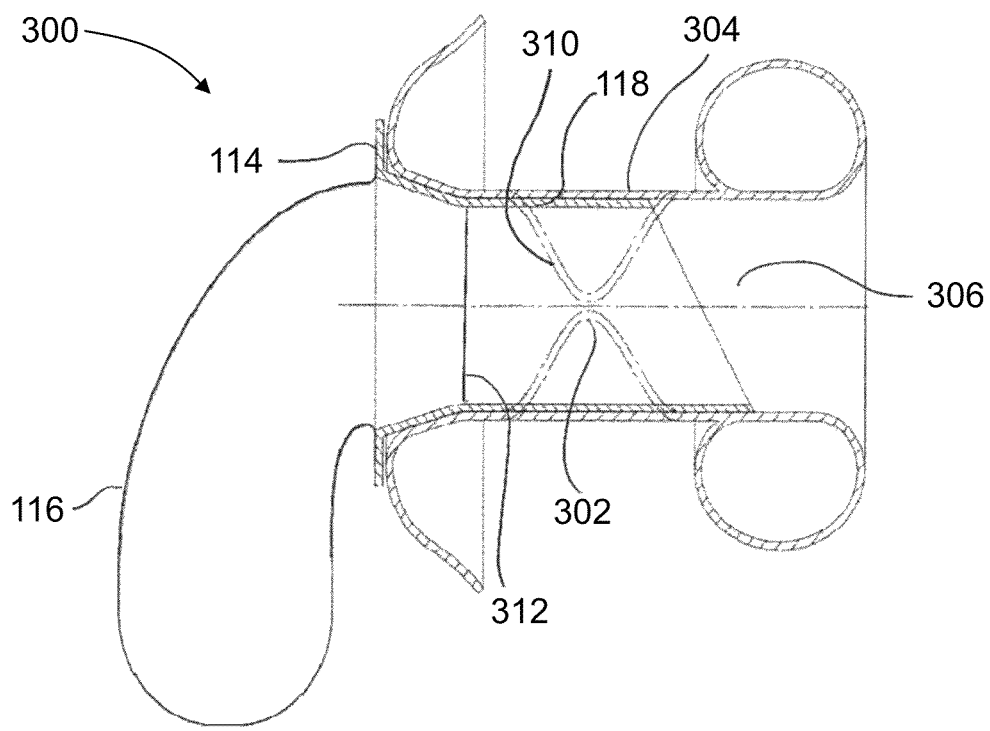
FIG. 3B schematically illustrates the valve mechanism in an open state, according to another embodiment of the present invention.

Reference is made to FIG. 3A which schematically illustrates an exemplary valve mechanism 300 including an elastically constricted portion 302 in an ostomy port 304, according to another embodiment of the present invention. Optionally, ostomy port 304 is used in an ileostomy. Optionally, semi-liquid waste does not pass constricted portion 302 and remains in a distal portion 306 of ostomy port 304. Optionally, solid waste content does not pass constricted portion 302 and remains in distal portion 306. Reference is also made to FIG. 3B which schematically illustrates valve mechanism 300 in an open state, according to another embodiment of the present invention.

In some exemplary embodiments, cap 114 and/or cannula 118 in FIGS. 1A, 1B may be used with ostomy port 304 for opening constricted portion 302, the closed mode of which is designated in FIG. 3B by dashed lines, for allowing waste content to reach a proximal opening 312. Optionally, cap 114 is inserted into proximal opening 312 so that cannula 118 penetrates distally into ostomy port 304 and into constricted portion 302, exerting a force radially outwards against an inner wall 310 for widening the constricted portion. Optionally, with constricted portion 302 open, waste content may flow from distal portion 306 through cap 114, including through cannula 118, into deployed ostomy bag 116. Optionally, removal of cap 114 will constrict portion 302.

Figure 4A:
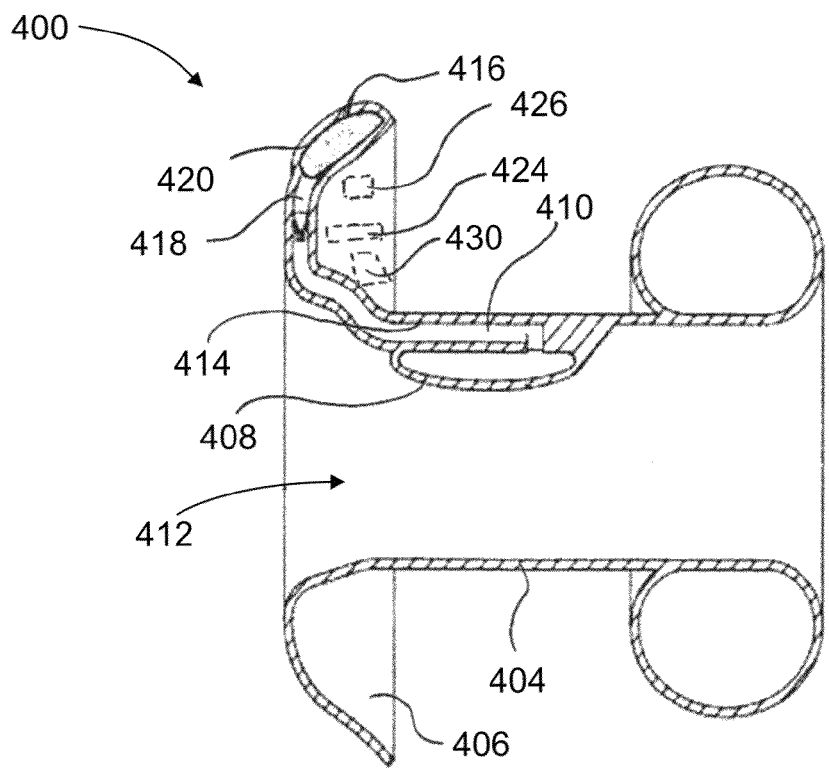
FIGS. 4A and 4B schematically illustrate an exemplary valve mechanism including an inflatable balloon and an inflator for sealing a proximal opening in an ostomy port, according to another embodiment of the present invention.
Figure 4B:
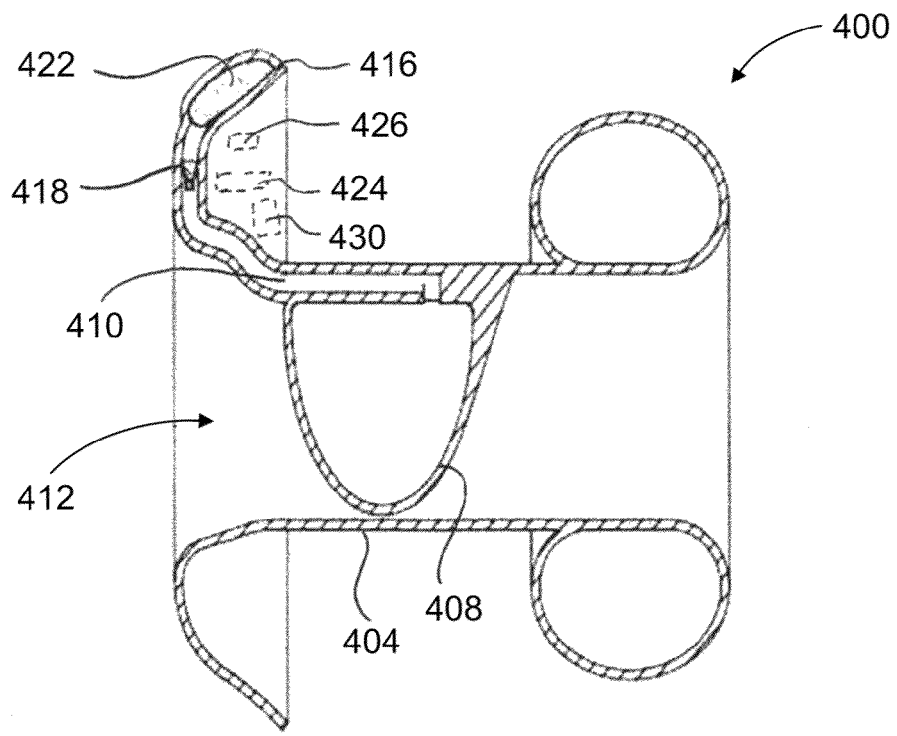

Reference is now made to FIGS. 4A and 4B which schematically illustrate an exemplary valve mechanism 400 including an inflatable section 408 and an inflator 416 for selectively sealing and unsealing a proximal opening 412 in an ostomy port 404, according to another embodiment of the present invention. Optionally, valve mechanism 400 is used with ostomy port 404 having a stomal cover 406. Optionally, proximal opening 412 is sealed while replacing an ostomy bag attached to ostomy port 404.

In an exemplary embodiment of the invention, valve mechanism 400 includes inflatable section, for example, elastic balloon 408 inside ostomy port 404 and inflator 416 in stomal cover 406. Optionally, balloon 408 is proximally positioned to proximal opening 412. Alternatively, balloon 408 is distally positioned from proximal opening 412. A lumen 410 along an inner wall 414 of ostomy port 404 fluidly connects inflator 416 with balloon 408. An inflation fluid 422 such as, for example air may be pumped through lumen 410 from inflator 416 into balloon 408 for inflating the balloon. Alternatively, water or other biocompatible, or cleansing, liquid fluid may be pumped through lumen 410 for inflating balloon 408. A check valve 418 is optionally connected to lumen 410 between inflator 416 and balloon 408 for regulating a pressure in balloon 408 when inflated. Optionally, check valve 418 is connected to a proximal end of lumen 410 proximally to inflator 416. Optionally, check valve 418 enables inflation fluid reflux through the valve for deflating balloon 408.

In some exemplary embodiments, balloon 408 is maintained in a deflated mode, as shown in FIG. 4A, for allowing waste content to reach proximal opening 412. Optionally, a cap (not shown) seals proximal opening 412 with balloon 408 deflated, and is removed for discharging the waste content into the ostomy bag attached to the cap. Optionally, when the ostomy bag is to be replaced, balloon 408 is inflated, as shown in FIG. 4B, for preventing waste content from reaching proximal opening 412 while the ostomy bag is being replaced.

In some exemplary embodiments, inflator 416 is inside a cavity 420 in stomal cover 406. Optionally, manually pumping inflator 416 through stomal cover 406 pumps inflation fluid 422 into balloon 408. Optionally, inflator 416 includes an internal volume adequate for storing the amount of inflation fluid 422 required to inflate balloon 408. Additionally or alternatively, a reservoir 424 is included in stomal cover 406 for holding inflation fluid 422. Reservoir 424 is optionally refillable with inflation fluid 422. Optionally, use of reservoir 424 substantially eliminates use of reflux in check valve 418. Deflating of balloon 408 may be done through a user-activated valve 430 which enables the user to deflate the balloon only after the bag is replaced. Alternatively, inflator 416 is electrically operated and includes a battery 426 in stomal cover 406. Alternatively, inflator 416 is automatic.

Figure 5:
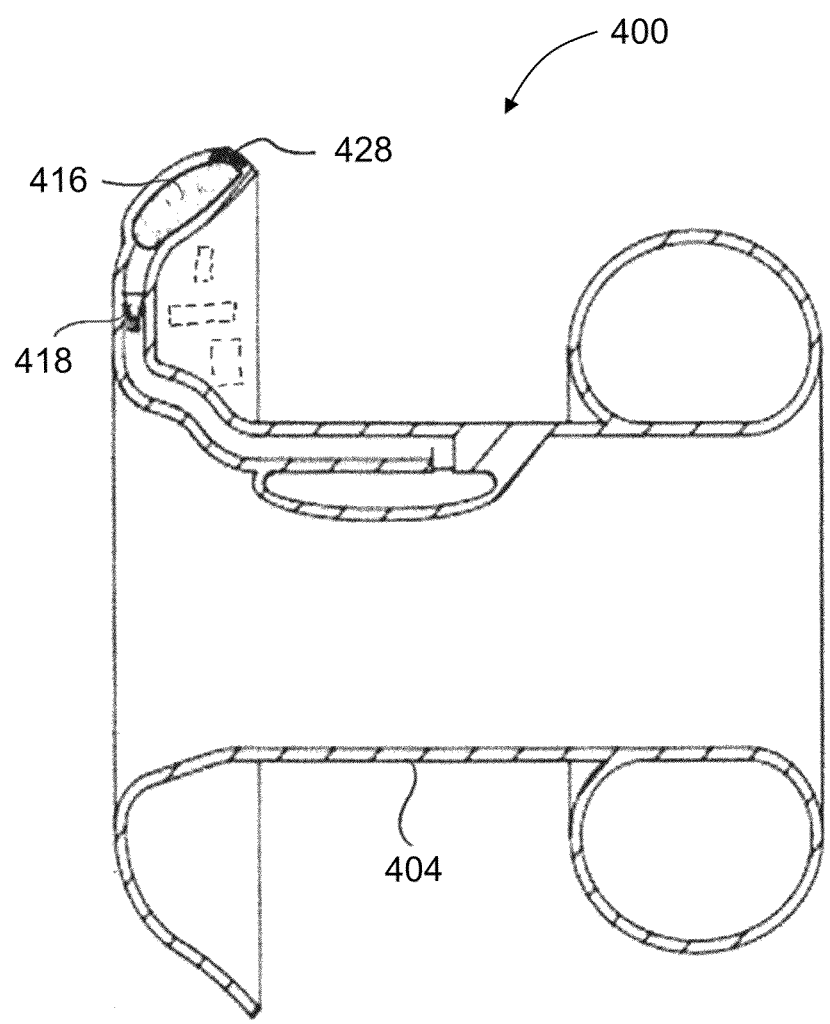
FIG. 5 schematically illustrates the valve mechanism of FIGS. 4A and 4B including an additional check valve, according to some embodiments of the present invention.

In some exemplary embodiments, valve mechanism 400 includes a check valve 428, in addition to check valve 418, for replenishing air in inflator 416, as shown in FIG. 5. Optionally, use of check valve 428 substantially eliminates use of reflux in check valve 418. Optionally, use of check valve 428 substantially eliminates possible use of reservoir 424. Optionally, user activated valve 430 is used for deflating balloon 408.

Figure 6:
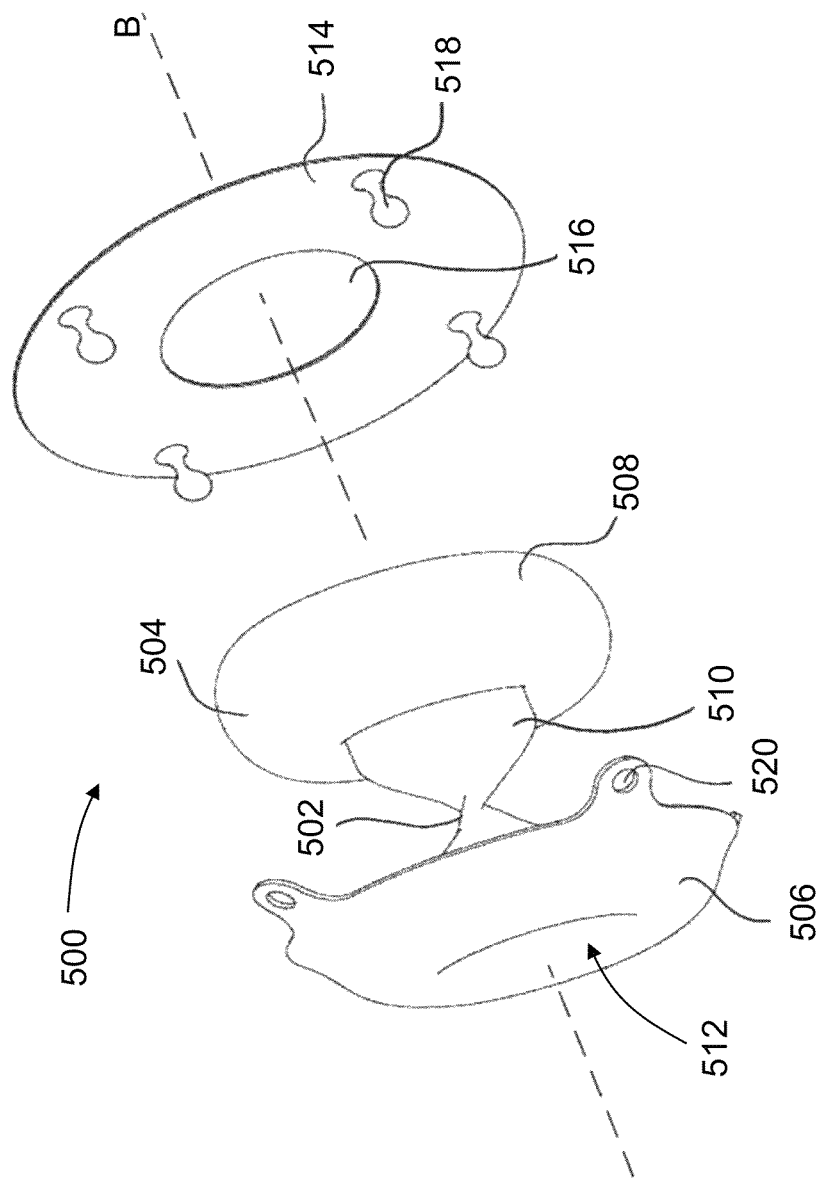
FIG. 6 schematically illustrates an exemplary valve mechanism including an elastic twistable portion for sealing a proximal port in an ostomy port, according to another embodiment of the present invention.

Reference is made to FIG. 6 which schematically illustrates an exemplary valve mechanism 500 including an elastic twistable portion 502 for sealing a proximal opening 512 in an ostomy port 504, according to another embodiment of the present invention. Ostomy port 504 includes a stomal cover 506 proximally connected in the port, a retention balloon 508 distally connected to the port, and a conduit 510 interconnecting the stomal cover and the balloon and including twistable portion 502. Waste content may be prevented from reaching proximal opening 512 by twisting stomal cover 506 about a central axis B of the ostomy port while balloon 508 remains fixed relative to central axis B. This results in a constriction being formed in conduit 510 at twistable portion 502, preventing waste content flow therethrough.

Valve mechanism 500 includes a flange 514 including an opening 516 which is attached to the external abdominal wall of the user around the stoma. Flange 514 includes fastening pins 518 for engaging openings 520 in stomal cover 506 when the stomal cover is twisted. Optionally, fastening pins 518 engage opening 520 when stomal cover 506 is not twisted. Engagement of fastening pins 518 with openings 520 prevents untwisting of stomal cover 506 from a twisted position, allowing the constriction in twistable portion 502 to be maintained.

In an exemplary use of valve mechanism 500, optionally, the user, prior to removing an ostomy bag, twists stomal cover 506 to create the constriction in twistable portion 502. Optionally, the user then engages openings 520 with fastening pins 518 on flange 514 while stomal cover 506 is in the twisted position. Optionally, once engaged, the user proceeds to remove and replace the ostomy bag. Optionally, following bag replacement, the user disengages openings 520 from fastening pins 518, allowing stomal cover to resume its untwisted position. Optionally, the user reengages openings 520 with fastening pins 518. Optionally, other types of fasteners may be used, for example a hook and loop mechanism.

Figure 7A:
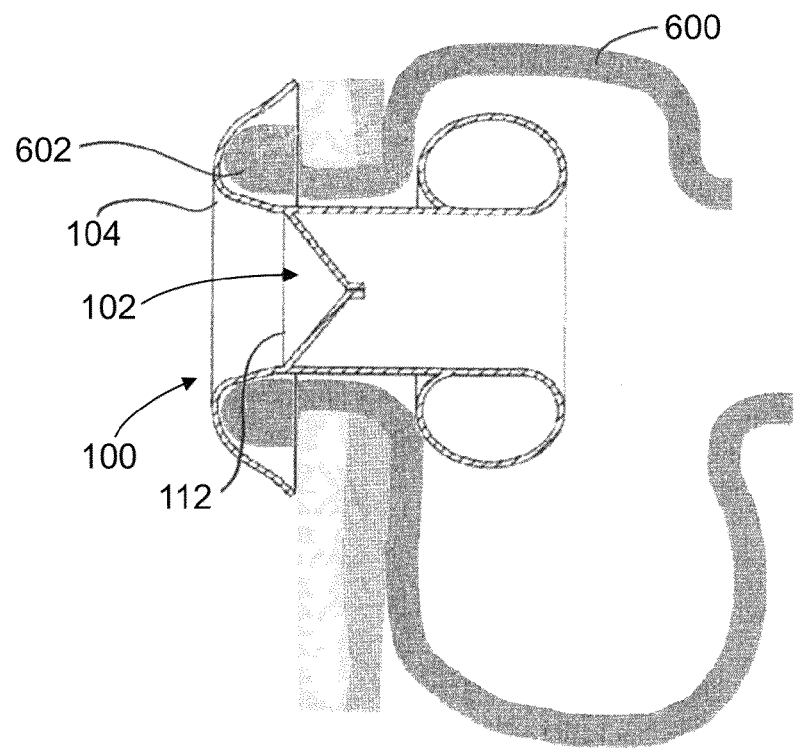
FIGS. 7A and 7B schematically illustrate the ostomy port and valve mechanism of FIGS. 1A and 1B inserted in an intestinal pouch, according to some embodiments of the present invention.
Figure 7B:
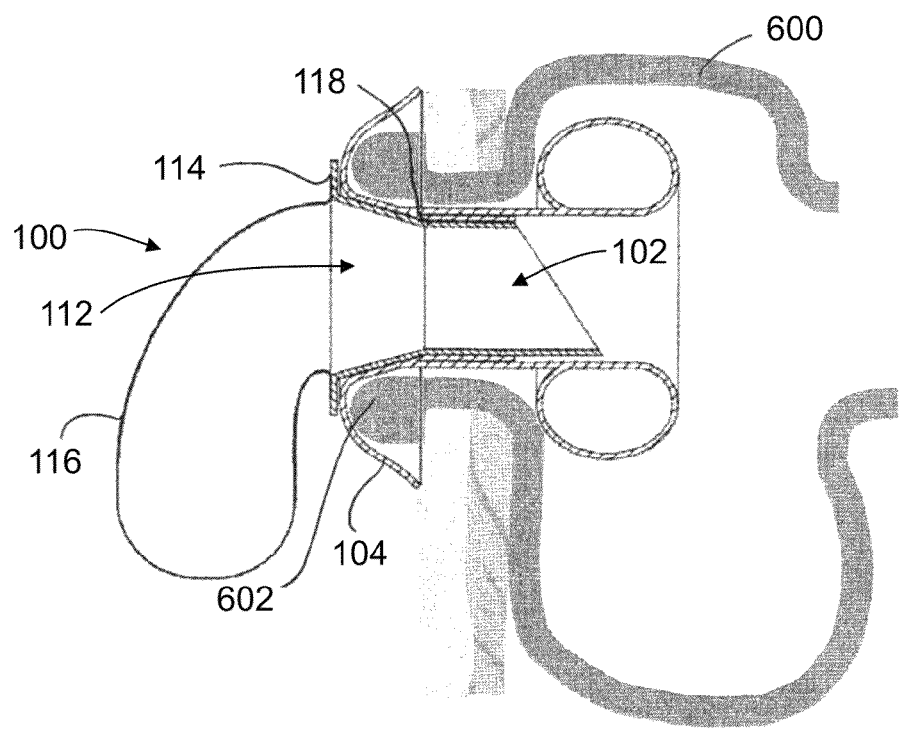

Reference is made to FIGS. 7A and 7B which schematically illustrate an ostomy port 104 having a valve mechanism 100 inserted in an intestinal pouch 600, according to some embodiments of the present invention. Optionally, intestinal pouch 600 is a Koch pouch. Alternatively, intestinal pouch 600 is an Indiana pouch. Ostomy port 104 may include a valve mechanism 200. Alternatively, ostomy port 304 including valve mechanism 300 is insertable in pouch 600. Alternatively, ostomy port 404 including valve mechanism 400 is insertable in pouch 600. Alternatively, ostomy port 504 including valve mechanism 500 is insertable in pouch 600.

In FIG. 7A, ostomy port 104 is inserted through a stoma 602 into intestinal pouch 600 in a configuration wherein waste content from intestinal pouch 600 is prevented from flowing out proximal opening 112. Valve mechanism 100 includes blocking element 102 in the closed position sealing proximal opening 112.

In FIG. 7B, ostomy port 104 is inserted through stoma 602 into intestinal pouch 600 in a configuration for evacuating waste content from the pouch. Cap 114 including cannula 118 is inserted through proximal opening 112, the cannula forcing open blocking element 102. Waste content flows from pouch 600 through cannula 118 and cap 114 into ostomy bag 116.

Figure 8:
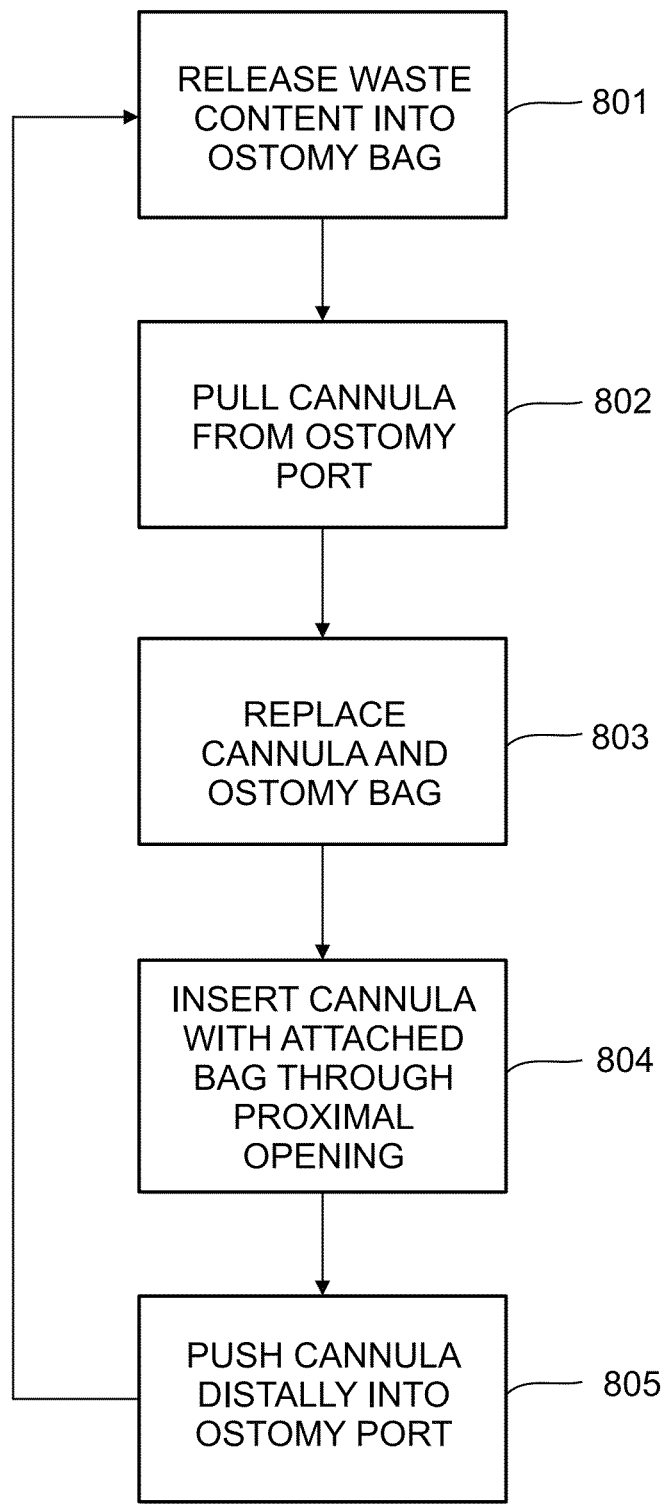
FIG. 8 illustrates a flow graph of an exemplary method of replacing an ostomy bag attached to an ostomy port, according to some embodiments of the present invention.

Reference is made to FIG. 8 which illustrates a flow graph of an exemplary method of replacing an ostomy bag attached to an ostomy port, according to some embodiments of the present invention. In describing the method, reference is made to the embodiment described and shown in FIGS. 1A and 1B.

At 801, optionally, the user discharges waste content into ostomy bag 116 attached to ostomy port 104. Optionally, the ostomy bag 116 is furled up inside a cap 114. Optionally, the user releases a plug on cap 114 allowing ostomy bag to unfurl outwards and receive the waste content discharged through ostomy port 104.

At 802, optionally, following discharge, the user pulls cannula 118 from ostomy port 104 through proximal opening 112. As cannula 118 is withdrawn from ostomy port 104 the force exerted by the cannula on flaps 108 in blocking element 102 is withdrawn. Optionally, flaps 108 abutting inner wall 110 revert to closed position, sealing proximal opening 112. Optionally, bag 116 is attached to cannula 118 and is detached from ostomy port 104 together with the cannula. Additionally or alternatively, bag 116 is attached to cap 114 and together removed from ostomy port prior to removal of cannula 118. Optionally, cannula 118 is attached to cap 114 and is removed together with the cap. Alternatively, cannula 118 is not attached to cap 114 and is removed following cap removal.

At 803, optionally, the user replaces removed cannula 118 with a new cannula 118. Optionally, a new bag 116 is attached to new cannula 118. Alternatively, the user attaches a new bag 116 to new cannula 118. Alternatively, the user uses the removed cannula 118 and replaces bag 116. Optionally, the user replaces removed cap 114 with a new cap 114. Optionally, new cap 114 includes new cannula 118 and new bag 116. Alternatively, new cap 114 includes new bag 116.

At 804, optionally, the user inserts a distal end of cannula 118 through proximal opening 112. Optionally, bag 116 is attached to a proximal end of cannula 118. Optionally, cannula 118 is attached to cap 114.

At 805, optionally, cannula 118 is pushed through proximal opening 112 distally into ostomy port 104. Cannula 118 pushes on blocking element 102 bending flaps 108 until abutting interior wall 110. Waste content may flow through cannula 118 to proximal opening 112. Optionally, cannula 118 is attached to cap 114, and cap 114 is sealingly fitted into proximal opening 112. Return to 801.

The terms "comprises", "comprising", "includes", "including", "having" and their conjugates mean "including but not limited to".

The term "consisting of" means "including and limited to".

The term "consisting essentially of" means that the method or structure may include additional steps and/or parts, but only if the steps and/or parts do not materially alter the basic and novel characteristics of the claimed method or structure.

As used herein, the singular form "a", "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An ostomy port comprising:
   a waste channel configured to and positioned so that it extends through the abdominal wall and a valve for selectively blocking and unblocking said waste channel; wherein
   said valve is positioned within said channel between and spaced from distal and proximal ends thereof, said distal end being deeper within the body than said proximal end;
   said valve comprises a portion which, in an uncovered blocking configuration, blocks the channel and resists the pressure of waste pushing proximally;
   said unblocks said channel upon distal deflection of said valve portion by pressing from a cover portion insertable to said channel from a proximal direction; and
   said valve, in said blocking configuration, opens by deflection of said valve portion proximally when a pressure exerted in a proximal direction by waste content in said waste channel is higher than a predetermined safety threshold.

2. The ostomy port according to claim 1, wherein said valve comprises a shutter valve which is opened by axial force along said channel in a direction towards the body.

3. The ostomy port according to claim 2, wherein said valve comprises an expandable element.

4. The ostomy port according to claim 2, wherein said port includes one or both of a reservoir of fluid and a pump for causing inflation of a chamber associated with said expandable element.

5. The port according to claim 2, wherein said valve is automatically activated to unblock said channel when said channel is covered by a suitable cover or bag.

6. The ostomy port according to claim 2, wherein said valve comprises a plurality of flaps.

7. The ostomy port according to claim 6, wherein said valve comprises an expandable element.

8. The ostomy port according to claim 6, wherein said port includes one or both of a reservoir of fluid and a pump for causing inflation of a chamber associated with said expandable element.

9. The port according to claim 6, wherein said valve is automatically activated to unblock said channel when said channel is covered by a suitable cover or bag.

10. The ostomy port according to claim 1, wherein said valve comprises an expandable element.

11. The ostomy port according to claim 10, wherein said port includes one or both of a reservoir of fluid and a pump for causing inflation of a chamber associated with said expandable element.

12. The port according to claim 10, wherein said valve is automatically activated to unblock said channel when said channel is covered by a suitable cover or bag.

13. The ostomy port according to claim 10, wherein said port includes one or both of a reservoir of fluid and a pump for causing inflation of a chamber associated with said expandable element.

14. The port according to claim 13, wherein said valve is automatically activated to unblock said channel when said channel is covered by a suitable cover or bag.

15. The ostomy port according to claim 1, wherein said valve is configured to automatically block said channel when at least one of one of a cover and a bag on said channel and comprising said cover portion is removed.

16. The port according to claim 15, wherein said valve is automatically activated to unblock said channel when said channel is covered by a suitable cover or bag.

17. The ostomy port according to claim 15, wherein said at least one of a cover and a bag includes a tube comprised in said cover portion which, when inserted into said channel, opens said valve and, when removed form said channel, allows said valve to self-close.

18. The port according to claim 1, wherein said valve is automatically activated to unblock said channel when said channel is covered by a suitable cover or bag.

19. The ostomy port according to claim 1, comprising a manual actuator for at least one of opening and closing said valve.

20. The port according to claim 1, wherein said predetermined safety threshold is between 70 and 200 mmHg.

21. A method for regulating waste content flow through a waste channel configured to and positioned so that it extends through the abdominal wall in an ostomy port comprising:
  closing a valve to block said channel in a valve configuration resisting the pressure of waste pushing proximally upon said valve;
  uncovering a proximal opening of said channel;
  allowing said pressure of waste pushing proximally upon said valve to increase; and
  opening automatically said closed valve by deflection of a portion of said valve proximally upon pressure exerted in a proximal direction by said waste content in said waste channel being higher than a predetermined safety threshold;
  wherein said closing a valve comprises automatically closing said valve by said uncovering;
  wherein said port has a cover including an elongate element which maintains said valve in an open configuration when inserted in said channel, and wherein said uncovering retracts said elongate element and allows said valve to close; and
  wherein said valve is positioned within said channel between and spaced from distal to proximal ends of the channel, said distal end deeper within the body than said proximal end.

22. The method according to claim 21, comprising attaching a bag or a cover to said port, said attaching automatically opening said valve.

23. The method according to claim 21, comprising manually closing said valve.

24. The method according to claim 21, comprising irrigating said waste channel.

25. An ostomy port having a waste channel configured to and positioned so that it extends through the abdominal wall comprising:
  said valve is positioned within said channel between and spaced from distal and proximal ends thereof, said distal end being deeper within the body than said proximal end;
  an inflatable section inside said waste channel, between and spaced from distal and proximal ends thereof, said distal end being deeper within the body than said proximal end, and said section being inflatable to a degree sufficient to block said channel and deflatable to a degree whereby it does not block or interfere with flow in said channel; and
  an integral inflator configured for pumping to selectively inflate said inflatable section to block said channel
  wherein said port includes a reservoir for holding inflation fluid for said inflatable section.

26. The port according to claim 25, comprising a stomal cover and wherein said inflator is provided in or on said stomal cover.

27. The port according to claim 25 including a check valve for regulating pressure in said inflatable section.

28. The port according to claim 27, wherein said check valve is suitable for deflation of said inflatable section.

29. The port according to claim 25, wherein said inflator comprises an air pump.

30. The port according to claim 25, comprising a deflation valve.

31. The port according to claim 25, wherein said inflator is electrically operated and activated by one or both of covering and uncovering of said port, using a covering or uncovering sensing circuit.

32. The port according to claim 25, including an indicator indicating one or both of when said channel is blocked and when said channel is open.

33. The port according to claim 32, wherein said indicator is a visual or acoustic display electrically activated by a sensing element which senses a state of said valve.

34. The port according to claim 25, wherein said inflator is electrically operated and includes a battery for powering said electrically operated inflator.

* * * * *